US00PP14663P39

(12) United States Plant Patent

Pouw

(10) Patent No.: US PP14,663 P3
(45) Date of Patent: Apr. 6, 2004

(54) HYBRID TEA ROSE PLANT NAMED 'RUIVONK'

(50) Latin Name: *Rosa hybrida v. Rosa L.*
Varietal Denomination: Ruivonk

(75) Inventor: Anton Pouw, De Kwakel (NL)

(73) Assignee: De Ruiter's Nieuwe Rozen B.V. (NL)

( * ) Notice: Subject to any disclaimer, the term of this patent is extended or adjusted under 35 U.S.C. 154(b) by 91 days.

(21) Appl. No.: 10/004,187

(22) Filed: Oct. 31, 2001

(65) Prior Publication Data

US 2002/0148012 P1 Oct. 10, 2002

(51) Int. Cl.[7] ..... A01H 5/00
(52) U.S. Cl. ..... Plt./137
(58) Field of Search ..... Plt./130, 137, 138

*Primary Examiner*—Howard J. Locker
(74) *Attorney, Agent, or Firm*—Christie, Parker & Hale, LLP

(57) ABSTRACT

A new and distinct Hybrid Tea Rose plant having attractive light pink flowers.

2 Drawing Sheets

CROSS-REFERENCE TO RELATED APPLICATION(S)

This Patent Application claims priority of European Patent Application No. 2000/1930, Certificate No. EU7944, dated Jul. 16, 2001 and Patent Application filed in The Netherlands, Application No. ROO2714, Certificate No. 19668, dated Apr. 6, 2001.

BACKGROUND OF THE INVENTION

The present invention relates to a new and distinct variety of rose plant of the Hybrid Tea rose class Botanical Classification Rosa L., male and female parents are unknown. The varietal denomination of this new rose is named 'Ruivonk.' The new variety was grown from a seed in The Netherlands.

SUMMARY OF THE INVENTION

Among the novel characteristics possessed by this new variety which distinguishes it from all varieties of which I am aware is its attractive flowers and large vase life.

Reproduction by propagation by cuttings of the new variety as performed in De Kwakel, The Netherlands shows that the foregoing and other distinguishing characteristics come true to form and are established and transmitted through succeeding propagation.

BRIEF DESCRIPTION OF ILLUSTRATION(S)

The accompanying illustrations show a typical specimen of the new variety depicted in color as nearly true as is reasonably possible to make the same in a color illustration of this character.

Figure 1:
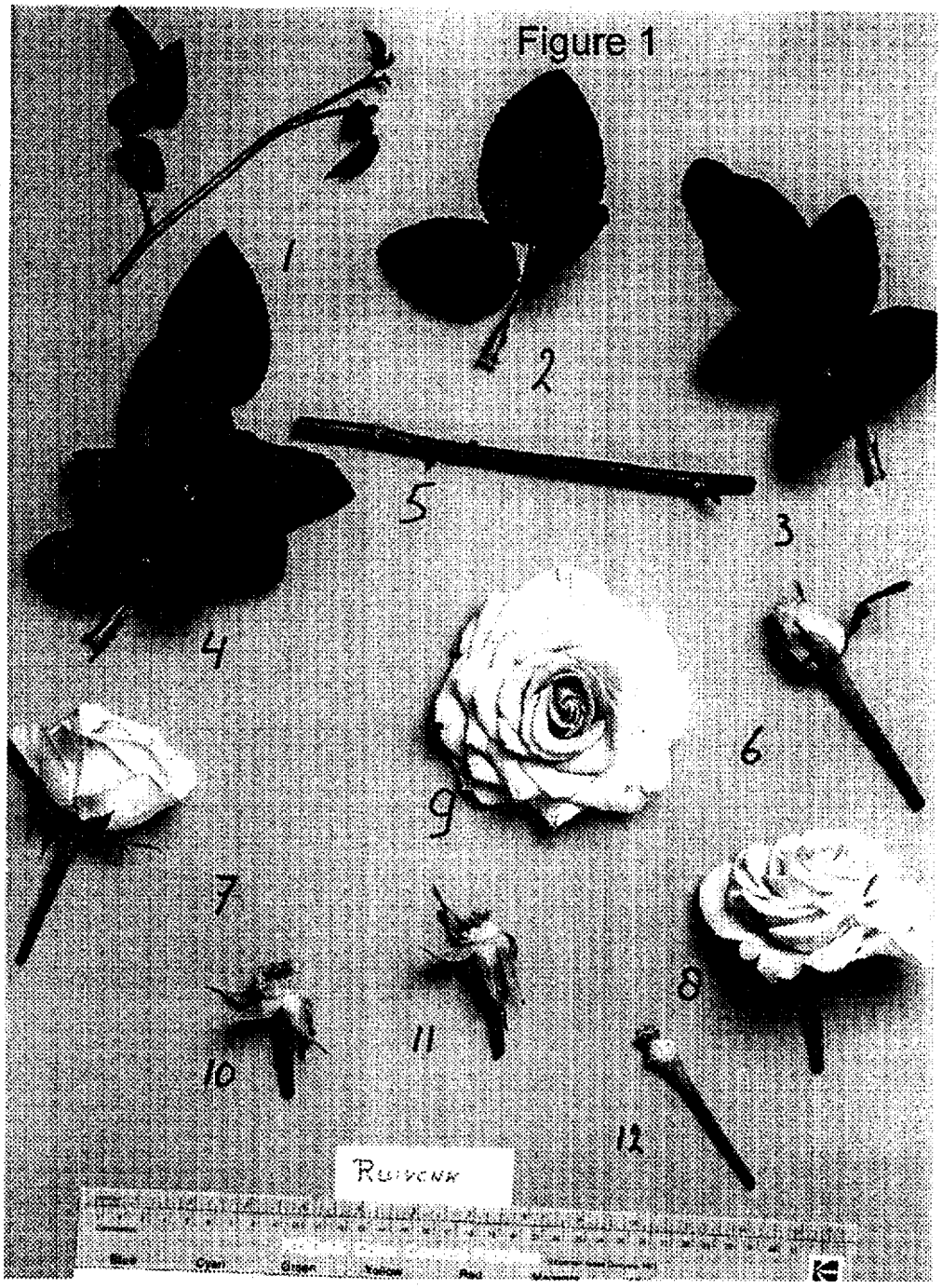

In FIG. 1, there is shown a young shoot 1; compound 3, 5, and 7 leaves, 2, 3 and 4; a stem segment without leaves 5; a flower bud after sepals open 6; flowers in different stages of development, 7, 8 and 9; and reproductive organs 10, 11 and 12.

Figure 2:
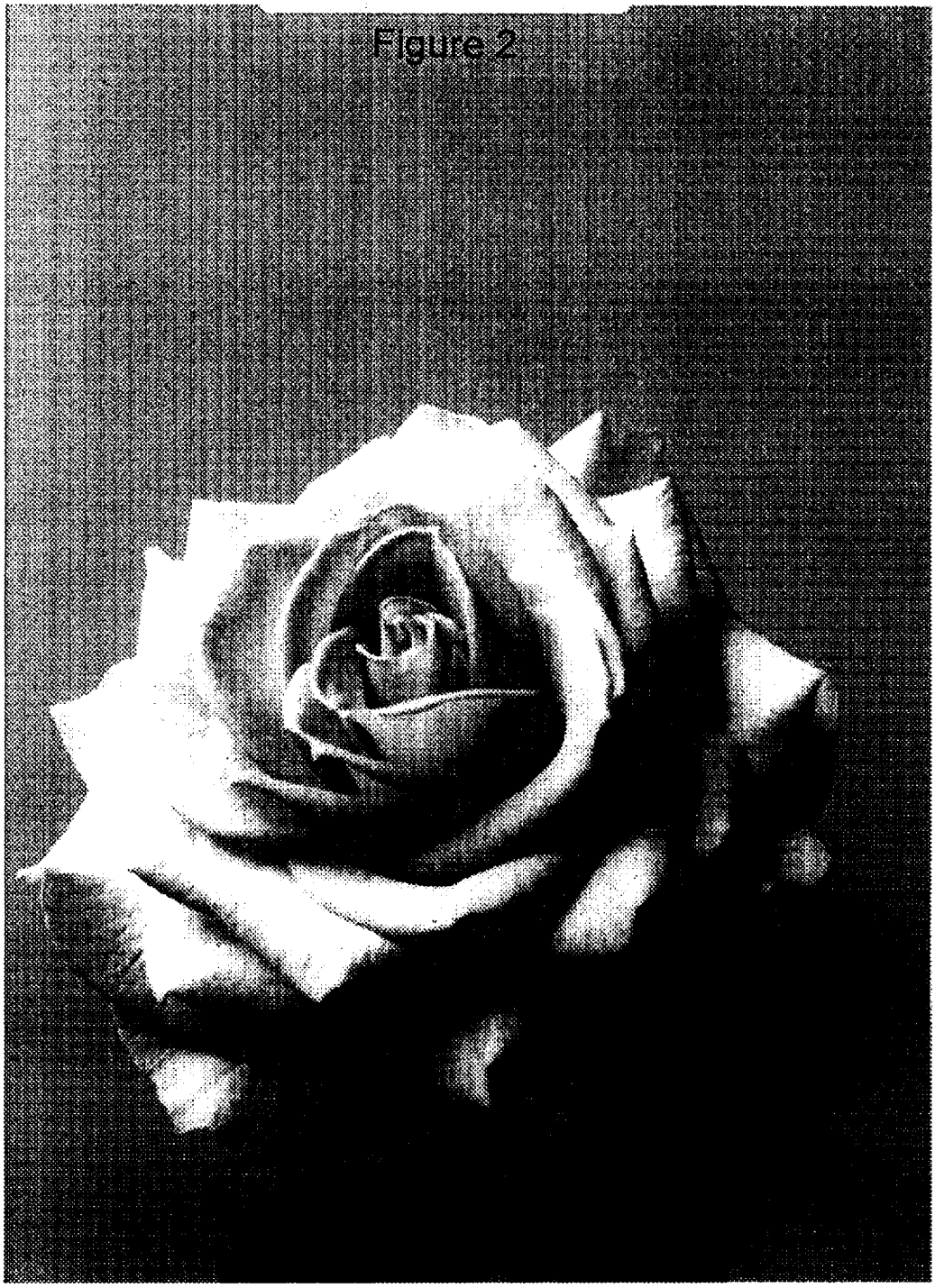

FIG. 2 shows a bloom of the new variety.

DESCRIPTION OF THE NEW VARIETY

The following is a detailed description of the new variety with color terminology in accordance with The Royal Horticultural Society Colour Chart (R.H.S.C.C). The terminology used in color description herein refers to plate numbers in the aforementioned color chart. Phenotypic expression may vary with light availability, environmental and cultural conditions.

The following observations are made of 9-month old plants grown in a greenhouse in De Kwakel, The Netherlands during September from a rooted cutting.

FLOWER

Blooming habit: Continuous; plants produce about 180 stems per $m^2$ per year in The Netherlands in a glasshouse in the Netherlands.

Bud: Large, width about 4 cm, height about 5 cm.
- *Form.*—Ovoid.
- *Color.*—When sepals first divide, light pink near 56D; with some green on the margin of the petals, near 145C.

Sepals: Usually 3 sepals without projections and 2 sepals with some leaf-like projections, top is pointed, surface appearance is woolly.
- *Size.*—Length about 3.5 cm, width at the base about 1 cm.
- *Color.*—Upper Surface: Near 144A. Under surface: Near 144A and 176B.
- *Peduncle.*—Length: About 8 cm. Aspect: Smooth, erect. Color: Near 143A.
- *Bracts.*—None observed.

Bloom:
- *Size.*—Average size when fully opened — about 12 cm.
- *Borne.*—Singly.
- *Form.*—Top is flat then becoming flattened convex; at maturity petals are slightly curled.
- *Petalage.*—Number of petals — about 45. Color (⅓ to ½ open) Outer Petals: Top surface — marginal zone near 62C, middle zone near 155A; Under surface — marginal zone between 62C and 62D middle zone near 155A. Inner Petals: Top surface — marginal zone between 62A and 62B, middle zone near 155A; Under surface — marginal zone near 62C, middle zone near 155A.
- *General tonality from a distance.*—Light pink.
- *Base of petals (point of attachment).*—Near 9C.

Color (fully opened):

*Outer petals.*—Top surface — marginal zone near 62B, middle zone near 155; under surface — marginal zone near 62C, middle zone near 155B.

*Inner petals.*—Top surface — marginal zone near 62A, middle zone near 155A; under surface — marginal zone near 62D, middle zone near 155A.

*General tonality from a distance.*—Light pink.

*Base of petals (point of attachment).*—Near 9C.

*Color change.*—As bloom ages, colors lighten from between 62A and 62B to near 62D.

*General tonality from a distance.*—Light Pink.

*Petal texture.*—Thick.

*Appearance.*—Smooth.

*Petal form.*—Round, cross section about 5 cm; petals are slightly curled.

Arrangement: Imbricated.

Petaloids in center: About 10; petaloid coloration is the same as the coloration of petals.

Persistence: Petals are persistent.

*Fragrance.*—None. Lasting quality On the plant: Extremely long, more than 35 days due to persistence. In the vase: Extremely long, up to 35 days.

REPRODUCTIVE ORGANS

Stamens, filaments and anthers: Stamens are approximately 90 in number; filaments are about 0.8 to 1 cm in length, not all possess an anther; anthers are about 0.2 to 0.3 cm in length, all open at approximately the same time.

Arrangement: Regularly arranged around styles.

*Color.*—Stamens near 9C, filaments near 9C, anthers near 9A.

*Pollen.*—Color near 161D.

Styles: Bunched, medium length, about 0.8 cm, color near 51A.

Stigmas: Color near 155B.

Hips:

*Shape.*—Funnel shaped.

*Size.*—Length about 1 cm, width at top about 1 cm.

PLANT

Form: Upright.

Growth: Uniform branching, vigorous; height attained (first season) about 260 cm.

Foliage: Compound, 3 to 5 leaflets, sometimes 7 leaflets.

*Size.*—Terminal leaflet of 3 leaflet leaf about 8 cm long; 5 leaflet leaf terminal leaflet about 7 cm long; 7 leaflet leaf terminal leaflet about 6 to 7 cm long.

*Quantity.*—About 11 leaves per stem.

*Color.*—New foliage: Upper side near 187A mixed with near 137A; under side near 183B. Mature foliage: Upper side near 138B; under side near 138B.

*Shape.*—Elliptic.

*Texture.*—Upper side: Smooth, semi-glossy with deep-lying veins. Under side: Smooth, matte with high-lying veins.

*Edge.*—Serrated.

*Serration.*—Serrate.

Petiole: Top surface near 178A; under surface between 138B and 178A.

Stipules: Length about 1.5 cm, edge irregular serrated at both sides.

Auricle: Small pointed, length about 5 mm, width about 2 mm; color near 138B.

Rachis: Gully shaped, upright edge, rough.

Resistance to disease: Susceptible to Blackspot, Mildew and Rust.

WOOD

New shoots:

*Bark.*—Smooth, near 178A and 146D.

*Wood.*—Near 146B.

Old wood:

*Bark.*—Smooth, near 138A.

Flower stem: About 60 to 90 cm from last cut (including peduncle).

Thorns:

*Quantity.*—About 5 small thorns on basal canes at the base, few thorns on laterals from basal canes on about the lower half of the stem, no thorns on upper part of the stem.

*Form.*—Straight to downward curved, length about 0.7 cm, color (when young) near 183B and near 146D, position irregular.

*Prickles.*—None observed on main stalks.

Winter hardiness: Not known, grown in glasshouse.

Uniqueness: Vase life is extremely long, up to 35 days; attractive color.

I claim:

1. A new and distinct Hybrid Tea Rose plant of the variety substantially as shown and described.

* * * * *

1
2
3
4
5
6
7
8
9
10
11
12
Rubycrew